US010551060B2

(12) United States Patent
Berberoglu et al.

(10) Patent No.: US 10,551,060 B2
(45) Date of Patent: Feb. 4, 2020

(54) SYSTEMS AND METHODS FOR CONVERTING BIOMASS TO BIOCRUDE VIA HYDROTHERMAL LIQUEFACTION

(71) Applicant: Board of Regents, The University of Texas System, Austin, TX (US)

(72) Inventors: Halil Berberoglu, Austin, TX (US); Rhykka L. Connelly, Austin, TX (US); Joey Anthony, Austin, TX (US); Cody Bond, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 283 days.

(21) Appl. No.: 15/791,061

(22) Filed: Oct. 23, 2017

(65) Prior Publication Data

US 2018/0045407 A1 Feb. 15, 2018

Related U.S. Application Data

(62) Division of application No. 14/483,798, filed on Sep. 11, 2014, now Pat. No. 9,797,597.

(60) Provisional application No. 61/886,463, filed on Oct. 3, 2013.

(51) Int. Cl.
| *C12M 1/00* | (2006.01) |
| *F23G 5/027* | (2006.01) |
| *C10G 1/00* | (2006.01) |
| *C10G 1/06* | (2006.01) |
| *C12M 1/107* | (2006.01) |
| *C12P 5/02* | (2006.01) |

(52) U.S. Cl.
CPC .............. *F23G 5/027* (2013.01); *C10G 1/00* (2013.01); *C10G 1/065* (2013.01); *C12M 21/02* (2013.01); *C12M 21/04* (2013.01); *C12M 21/12* (2013.01); *C12M 43/00* (2013.01); *C12M 43/08* (2013.01); *C10G 2300/1003* (2013.01); *C10G 2300/1007* (2013.01); *C10G 2300/1011* (2013.01); *C10G 2300/1014* (2013.01); *C10G 2300/1018* (2013.01); *C12P 5/023* (2013.01); *F23G 2900/50803* (2013.01); *Y02E 20/12* (2013.01); *Y02E 50/14* (2013.01); *Y02E 50/343* (2013.01); *Y02P 20/129* (2015.11); *Y02P 20/134* (2015.11); *Y02P 20/136* (2015.11); *Y02P 30/20* (2015.11); *Y02W 10/37* (2015.05)

(58) Field of Classification Search
CPC .... C10G 3/40; C10G 3/52; C10G 2300/1003; C10G 2300/1007; C10G 2300/1011; C10G 2300/1014; C10G 2300/1018; C12M 21/02; C12M 21/04; C12M 21/12; C12M 43/00; C12M 43/08; F23G 5/027; F23G 2900/50803; C12P 5/023; Y02E 20/12; Y02E 50/14; Y02E 50/343; Y02P 20/129; Y02P 20/136; Y02P 30/20
See application file for complete search history.

(56) References Cited

U.S. PATENT DOCUMENTS

| 4,069,812 | A | 1/1978 | O'Neill |
| 9,006,502 | B2 | 4/2015 | Bosetti et al. |
| 2009/0082604 | A1 | 3/2009 | Agrawal et al. |
| 2010/0228062 | A1 | 9/2010 | Babicki et al. |
| 2011/0023565 | A1 | 2/2011 | Yanik et al. |
| 2011/0092726 | A1 | 4/2011 | Clarke |
| 2011/0294175 | A1 | 12/2011 | Bianchi et al. |
| 2012/0055077 | A1 | 3/2012 | Savage et al. |
| 2012/0172642 | A1 | 7/2012 | Bosetti et al. |
| 2013/0164812 | A1 | 6/2013 | Nicholas et al. |
| 2013/0167603 | A1 | 7/2013 | Bathurst et al. |
| 2017/0107478 | A1* | 4/2017 | Harmon ................ C12M 43/02 |
| 2019/0263700 | A1* | 8/2019 | Xu ......................... C02F 11/04 |

FOREIGN PATENT DOCUMENTS

| CN | 101805629 | 8/2010 |
| CN | 102192114 | 9/2011 |
| CN | 103339229 | 10/2013 |
| GB | 2073869 | 10/1981 |
| WO | 2011/030196 | 3/2011 |
| WO | 2011100696 A2 | 8/2011 |

(Continued)

OTHER PUBLICATIONS

English translation of Office Action dated May 24, 2018, from Chinese Application No. 201480062723.2, 19 pages.

(Continued)

*Primary Examiner* — Aaron J Kosar
(74) *Attorney, Agent, or Firm* — Meunier Carlin & Curfman LLC

(57) ABSTRACT

Systems and processes of providing novel thermal energy sources for hydrothermal liquefaction (HTL) reactors are described herein. According to various implementations, the systems and processes use concentrated solar thermal energy from a focused high-energy beam to provide sufficient energy for driving the HTL biomass-to-biocrude process. In addition, other implementations convert biowaste, such as municipal biosolids and grease and food waste, to biocrude using anaerobic digesters, and a portion of the biogas generated by the digesters is used to produce the thermal and/or electrical energy used in the HTL reactor for the biomass-to-biocrude process. Furthermore, alternative implementations may include a hybrid system that uses biogas and solar radiation to provide sufficient thermal energy for the HTL reactor.

24 Claims, 9 Drawing Sheets

(56) References Cited

FOREIGN PATENT DOCUMENTS

WO      2012117319      9/2012

OTHER PUBLICATIONS

International Search Report and Written Opinion, issued for PCT/US2014/055054, dated Feb. 10, 2015.
International Preliminary Report on Patentability and Written Opinion, issued for PCT/US2014/055054, dated Apr. 14, 2016.
Supplementary Search Report issued in European Application No. 14850244.6, dated May 4, 2017.
Demirbas, et al., "Competitive liquid biofuels from biomass", Applied Energy 88, 2011, 17-28.
Lede, et al., "Solar Thermochemical Conversion of Biomass", Solar Energy 65:1, 1999, 3-13.
Kalogirou, Progress in Energy and Combustion Science, 2004, 30, pp. 231-295.
Elliott, "Hydrothermal Processing" Thermochemical Processing of Biomass: Conversion into Fuels, Chemicals and Power, First Edition, Robert C. Brown (ed.), John Wiley & Sons, Ltd., 2011, chapter 7, p. 200-231. ISBN: 978-0-470-72111-7.
Pearce, "An integrated approach to Microalgae biomass generation and processing" Thesis, Cranfield University, Mar. 2016, 290pp.
Knorr, et al., "Production of Advanced Biofuels via Liquefaction Hydrothermal Liquefaction Reactor Design", Apr. 5, 2013, National Renewable Energy Laboratory (NREL)/ National Advanced Biofuels Consortium (NABC), Report 30352.00/01, 90pp.
Hoffmann, et al., "Conceptual design of an integrated hydrothermal liquefaction and biogas plant for sustainable bioenergy production", Bioresource Technology 129, 2013, 402-410.
Summary of Office Action from JP Associate in corresponding JP Application No. 2016-519929, dated Dec. 11, 2018.
Translation of Common Knowledge evidence, Handbook of Scientific Knowledge Necessary for Youth, pp. 350-353.
Communication Pursuant to Article 94(3) EPC in EP 14850244.6, dated Oct. 6, 2017.
Summary of Office Action from JP Associate in corresponding JP Application No. 2016-519929, dated Jul. 3, 2018.
Translation of Chinese Office Action issued in CN 201480062723.2, dated Nov. 23, 2019.

\* cited by examiner

SYSTEMS AND METHODS FOR CONVERTING BIOMASS TO BIOCRUDE VIA HYDROTHERMAL LIQUEFACTION

RELATED APPLICATIONS

This application is a divisional application of U.S. patent application Ser. No. 14/483,798, filed Sep. 11, 2014, which claims priority to U.S. Provisional Patent Application No. 61/886,463 filed Oct. 3, 2013 and entitled "Systems and Methods for Converting Biomass to Biocrude via Hydrothermal Liquefaction," the contents of which are each herein incorporated by reference in their entirety.

BACKGROUND

The Energy Independence and Securities Act of 2007 (EISA) established mandatory Renewable Fuel Standards (RFS) that require an increase from 9 billion gallons in 2008 to a minimum of 36 billion gallons of renewable fuels to be blended in transportation fuels sold in the US by 2022. Today, we face a challenge in meeting these mandates partly because of the energy requirements of generating advanced biofuels as well as sourcing an adequate supply of reliable feedstocks.

To date, the microalgae-to-renewable fuel pathway has focused on the generation of lipids within the microalgae, followed by the extraction and conversion of those lipids to biodiesel. The process relies on the microalgae to generate large concentrations of lipids in order to make the process energy return on investment (EROI) favorable. Since specific high lipid-yielding microalgae are selected for cultivation, contaminants such as other species of algae and predators only lower expected lipid yields. Thus, in practice, lipids yields have consistently been lower than predicted because of these factors.

The man-made process of hydrothermal liquefaction (HTL) of biomass-to-biocrude mimics the natural process of applying heat and pressure to decayed biomass in the earth's crust to form fossil fuel crude oil over the course of millennia. In this process, nearly all of the organic fraction (lipids, carbohydrates, protein, and nucleic acids) of the feedstock can be converted to biocrude, leading to much higher biomass-to-biocrude yields. FIG. 1 illustrates various types of biomass feedstocks that may be used to create biocrude via the HTL process, including cultured algae, marine biomass, food waste, wood waste, and animal waste. Biomass feedstocks may also include municipal biosolid waste and grease waste. Biomass-to-biocrude conversion rates have been reported to be in the 40%-50% range, with some rates as high as 65%.

However, one of the main barriers preventing the widespread adoption of the HTL technology to produce renewable fuels has been the high energy requirement to drive the HTL reactor, which requires temperatures of around 400° C. and pressures of around 20 MPa. Traditionally, the HTL process requires a prohibitively large energy input that in turn renders the process with a negative EROI. Furthermore, current HTL processes are conducted in batch mode.

BRIEF SUMMARY

Described herein are systems and processes of providing novel thermal energy sources for hydrothermal liquefaction (HTL) reactors. According to various implementations, the systems and processes use concentrated solar thermal energy from a focused high-energy beam to provide sufficient energy for driving the HTL biomass-to-biocrude process. In addition, other implementations convert biowaste, such as municipal biosolids and grease and food waste, to biocrude using anaerobic digesters, and a portion of the biogas generated by the digesters is used to produce the thermal and/or electrical energy used in the HTL reactor for the biomass-to-biocrude process. Furthermore, alternative implementations may include a hybrid system that uses biogas and solar radiation to provide sufficient thermal energy for the HTL reactor.

According to certain implementations, a system for converting biomass to biocrude includes a hydrothermal liquefaction reactor configured for converting biomass slurry to biocrude and a solar thermal energy collection system configured for providing concentrated solar thermal energy to the hydrothermal liquefaction reactor for heating the biomass slurry. The solar thermal energy collection system may include a solar thermal energy concentrating mechanism and a receiver. The solar thermal energy concentrating mechanism may be selected from the group comprised of a concave dish, a parabolic mirror, and a Fresnel lens, for example. The receiver is configured for receiving concentrated solar thermal energy from the solar thermal energy concentrating mechanism and may be operatively positioned adjacent the solar thermal energy concentrating mechanism. The hydrothermal liquefaction reactor may be disposed adjacent the receiver. For example, in one implementation, the hydrothermal liquefaction reactor includes a coiled conduit disposed within a housing of the receiver. In another implementation in which the hydrothermal liquefaction reactor is disposed remotely from the receiver, the system may include a heat transfer fluid configured for transferring at least a portion of the concentrated thermal energy from the receiver to the hydrothermal liquefaction reactor.

The system may also include a pump for continuously pumping the biomass slurry through the hydrothermal liquefaction reactor. For example, the pump may be configured for pumping the biomass slurry at a pressure around 20 MPa. In addition, the solar thermal energy collection system may be configured for heating the biomass slurry to about 400° C.

The system, according to some implementations, may also include a quencher disposed adjacent an exit of the hydrothermal liquefaction reactor that is configured for quickly cooling the biocrude and/or a heat exchanger upstream of the hydrothermal liquefaction reactor that is configured for harvesting the thermal energy from the biomass slurry. Furthermore, in certain implementations, the system may include a generator configured for generating electrical energy for at least one of one or more bioslurry pumps and one or more electrical components, wherein the thermal energy from the heat exchanger is used for driving the generator. In addition, some implementations of the system may also include two hydrothermal liquefaction reactors—a first hydrothermal liquefaction reactor and a second hydrothermal liquefaction reactor. The second hydrothermal liquefaction reactor is disposed downstream of the first hydrothermal liquefaction reactor and the heat exchanger, and the thermal energy from the heat exchanger is transferred to the second hydrothermal liquefaction reactor.

Other implementations include a process of converting biomass to biocrude that includes: (1) collecting thermal energy from a solar thermal energy concentrating mechanism; (2) pumping a slurry of biomass through a hydrothermal liquefaction reactor; and (3) heating, in the hydrothermal liquefaction reactor, the biomass slurry using the thermal energy collected from the solar thermal energy concentrating mechanism. Heating the biomass slurry may produce biocrude, biogas, and biochar. The process may further include: (1) quenching the biomass slurry after the biomass slurry exits the hydrothermal liquefaction reactor, and/or (2) harvesting thermal energy from combustion of one or more of the produced biocrude, biogas, and biochar. The harvested thermal energy may be used to power at least one electrical generator, which may be configured for supplying electrical energy to at least one pump for pumping the biomass slurry through the hydrothermal liquefaction reactor, and/or to supply additional thermal energy to the hydrothermal liquefaction reactor. Harvesting the thermal energy may be performed by a heat exchanger, according to certain implementations.

In addition, in implementations in which the biomass slurry includes microalgae, the process may further include: (1) cultivating the microalgae; (2) passing the cultivated microalgae through a pulsed electric field; (3) after passing through the pulsed electric field, passing the cultivated microalgae through an algae growth facility; (4) after passing through the algae growth facility, passing the cultivated microalgae through a pH-driven flocculation concentration process; and (5) passing the biocrude through a cross flow filtration mechanism for substantially removing phosphorus and polar components.

In other implementations in which the biomass includes municipal biowaste, the process may further include: (1) feeding the municipal biowaste to anaerobic digesters; (2) harvesting thermal energy from combustion of biogas generated by the anaerobic digesters; and (3) feeding a portion of the harvested thermal energy to a generator configured for generating electrical energy for operating the at least one pump.

Other various implementations include a system for converting biomass to biocrude that includes a hydrothermal liquefaction reactor configured for converting biomass slurry to biocrude and a generator configured for using at least a portion of thermal energy from combusted biogas for generating electrical energy. The generated electrical energy and any remaining thermal energy from the biogas combustion are provided to the hydrothermal liquefaction reactor for heating the biomass slurry. In certain implementations, the system may also include at least one anaerobic digester configured for digesting biosolid waste and producing the biogas. Furthermore, in some implementations, the system may also include a concentration mechanism configured for receiving the biosolids from the anaerobic digester and concentrating the biosolids prior to the biosolids being converted to biocrude by the hydrothermal liquefaction reactor. This system may be installed at least partially within a biosolids treatment facility, according to some implementations. And, the biogas may be harvested from the system or remotely from the system, according to certain implementations.

Other implementations include a system for converting biomass to biocrude that includes a hydrothermal liquefaction reactor configured for converting biomass slurry to biocrude and a generator configured for using a first portion of thermal energy from combusted biogas and a first portion of thermal energy captured by a solar thermal energy collection system for generating electrical energy. At least a portion of the generated electrical energy and second portions of the thermal energy from the biogas combustion and solar thermal energy collection system are provided to the hydrothermal liquefaction reactor for heating the biomass slurry.

According to various implementations, a process of converting biomass to biocrude includes: (1) collecting thermal energy from combustion of biogas; (2) pumping a slurry of biomass through a hydrothermal liquefaction reactor; and (3) heating, in the hydrothermal liquefaction reactor, the biomass slurry using the collected thermal energy. The biogas may be produced by at least one anaerobic digester of a biosolids treatment facility, for example. The process may further include: (1) collecting thermal energy from combustion of natural gas; and (2) heating the biomass slurry using the collected thermal energy from the combustion of natural gas in the hydrothermal liquefaction reactor.

Another process of converting biomass to biocrude includes: (1) feeding municipal sludge to at least one anaerobic digesters, the municipal sludge comprising biowaste; (2) collecting thermal energy from combustion of a first portion of biogas generated from partial digestion of the biowaste; (3) providing the thermal energy from combustion of the first portion of biogas to a generator; (4) collecting thermal energy from combustion of a second portion of biogas generated from partial digestion of the biowaste; (5) providing the thermal energy from combustion of the second portion of the biogas, waste heat generated by the generator, at least a portion of electrical energy generated by the generator, and partially digested biowaste solids effluent from the anaerobic digester to a hydrothermal liquefaction system; (6) recirculating waste heat generated by the hydrothermal liquefaction system to the anaerobic digesters; and (7) harvesting biochar and biocrude from the hydrothermal liquefaction system. The hydrothermal liquefaction system may include a pretreater and a reactor, according to certain implementations. In addition, the process may further include: (1) concentrating the biosolids fed from the anaerobic digester prior to feeding the biosolids to the hydrothermal liquefaction system, and (2) feeding an aqueous phase from the hydrothermal liquefaction system and washoff from the concentration of the biosolids to secondary and tertiary treatment streams of a biosolids treatment plant.

DETAILED DESCRIPTION

Described herein are systems and processes of providing novel thermal energy sources for hydrothermal liquefaction (HTL) reactors. For example, various implementations include a novel hydrothermal liquefaction (HTL) reactor that uses solar thermal concentration technology in a novel way such that the energy barrier for the HTL process is removed. According to various implementations, the systems and processes use concentrated solar thermal energy from a focused high-energy beam to provide sufficient energy for driving the HTL biomass-to-biocrude process. The concentrated solar thermal energy may be collected via various solar thermal energy concentrating mechanisms, including, for example, a concave dish, parabolic mirrors, and Fresnel lenses, and the solar thermal energy may be used directly or indirectly, such as via heat exchange fluids, by the HTL reactor.

In addition, other implementations convert biowaste, such as municipal biosolids and grease and food waste, to biocrude using anaerobic digesters, and a portion of the biogas generated by the digesters is used to produce the thermal and/or electrical energy used in the HTL reactor for the biomass-to-biocrude process. Furthermore, alternative implementations may include a hybrid system that uses biogas and solar radiation to provide sufficient thermal energy for the HTL reactor. These implementations are described in detail below.

Figure 1:
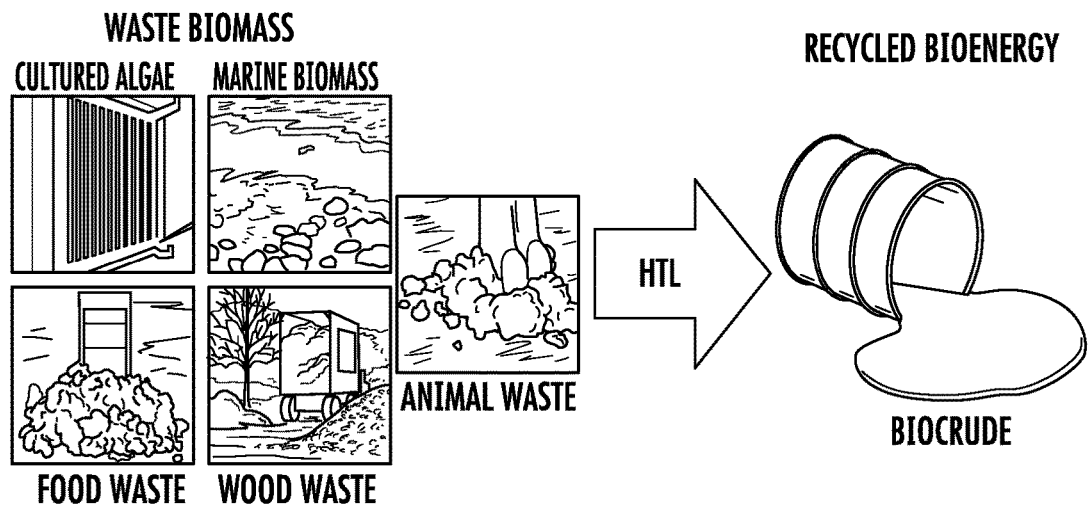
FIG. 1 illustrates a high level process flow of the HTL process.
Figure 2:
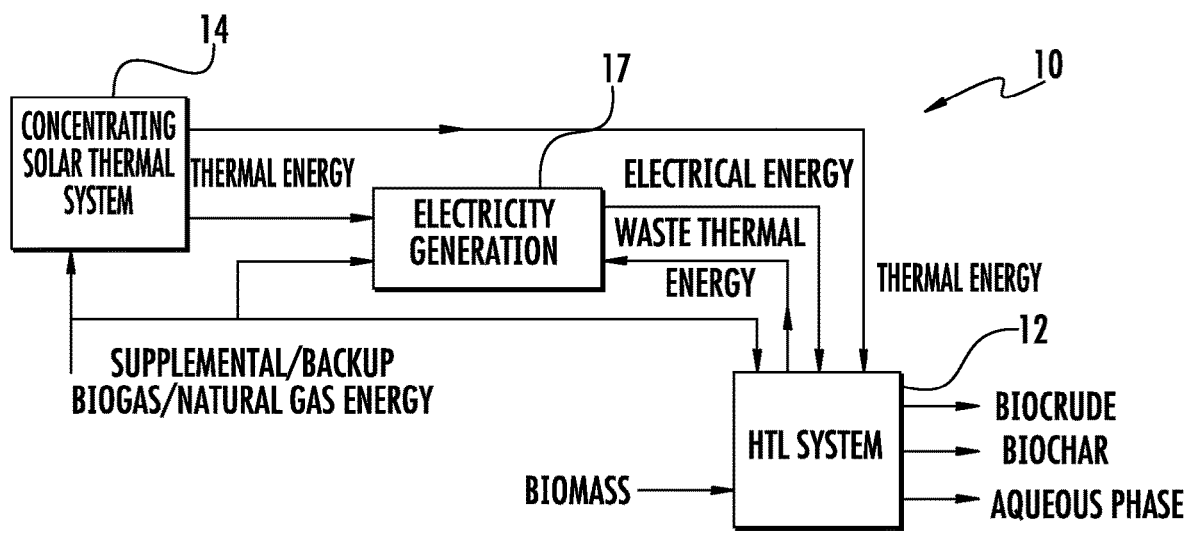
FIG. 2 illustrates a schematic diagram of an HTL system that uses solar radiation to provide thermal energy to the HTL reactor according to certain implementations.

FIG. 2 illustrates a schematic diagram of a system for converting biomass to biocrude that uses a solar radiation concentration mechanism to provide thermal energy to the HTL system, according to certain implementations.

In particular, the system 10 includes a hydrothermal liquefaction (HTL) system 12 and a solar thermal energy concentrating mechanism 14 configured for providing thermal energy to the hydrothermal liquefaction (HTL) system 12 for heating the biomass slurry. The system 10 also includes a generator 16 for generating electricity. The solar thermal energy concentrating mechanism 14 may be a concave dish, such as shown in FIGS. 3-6, but in other implementations, it may be a parabolic mirror or a Fresnel lens, for example. The solar thermal energy concentrating mechanism may be configured for heating the biomass slurry to about 400° C.

Figure 3:
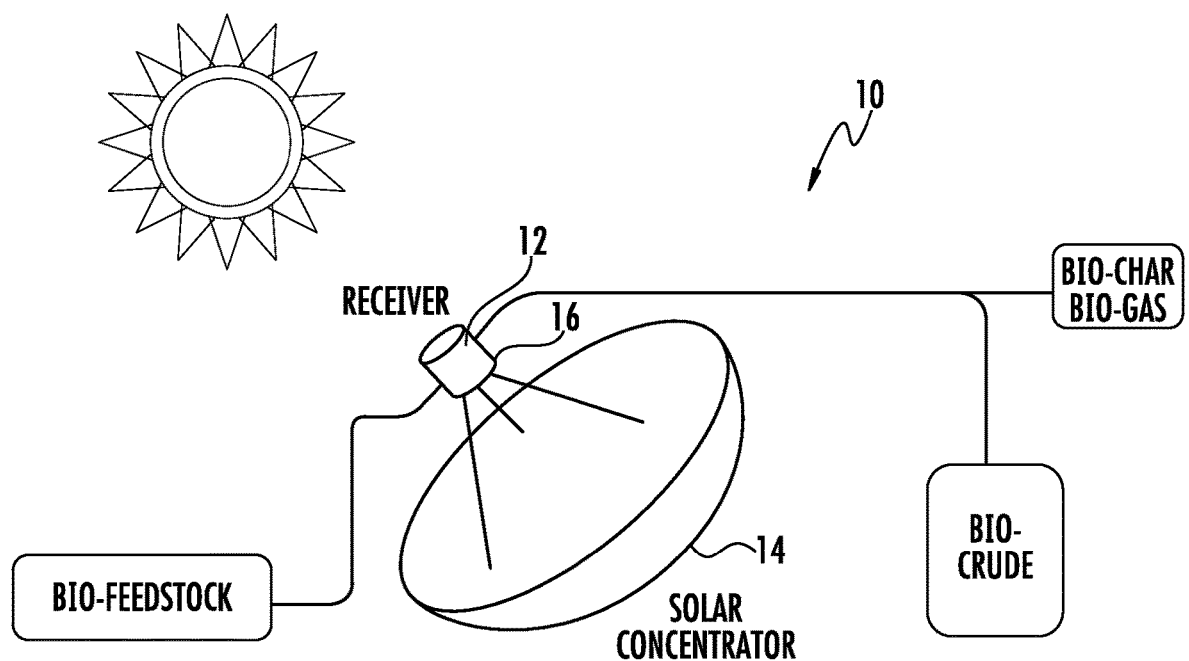
FIG. 3 illustrates an exemplary solar energy concentrating mechanism that may be used with the system of FIG. 2 according to one implementation.
Figure 4:
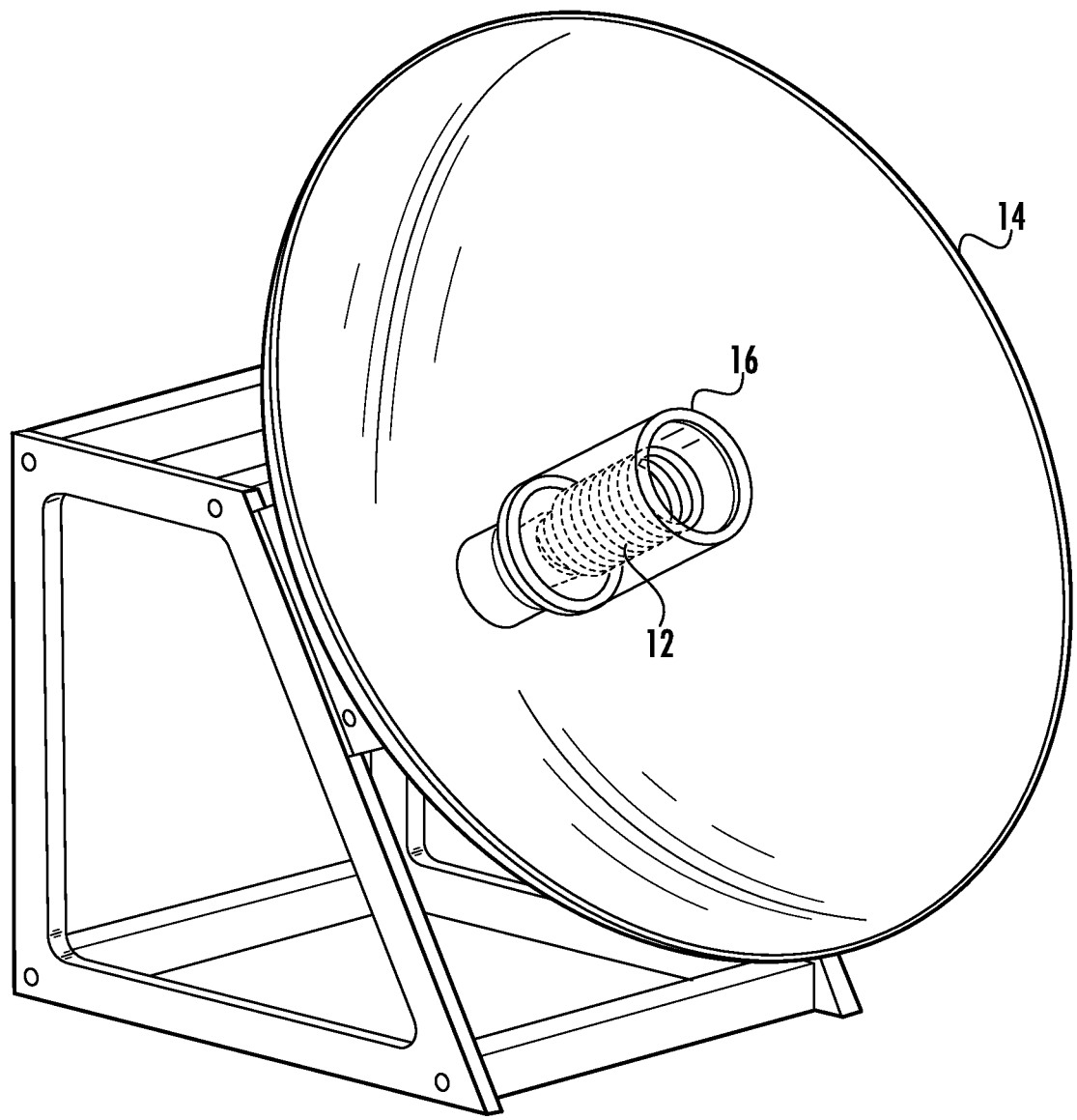
FIG. 4 illustrates a perspective view of the solar energy concentrating mechanism shown in FIG. 3.
Figure 5:
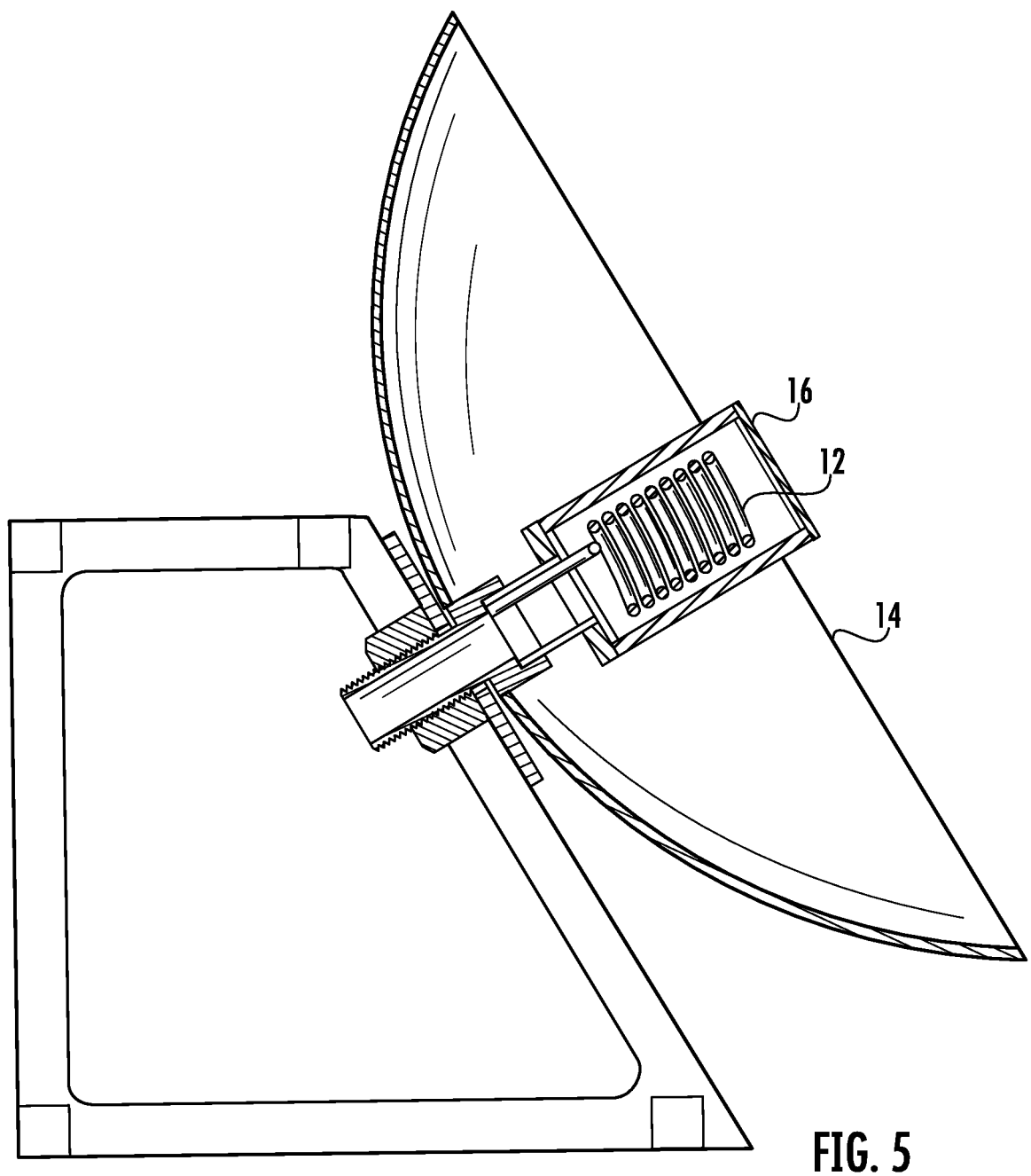
FIG. 5 illustrates a side view of the solar energy concentrating mechanism shown in FIG. 4.
Figure 6:
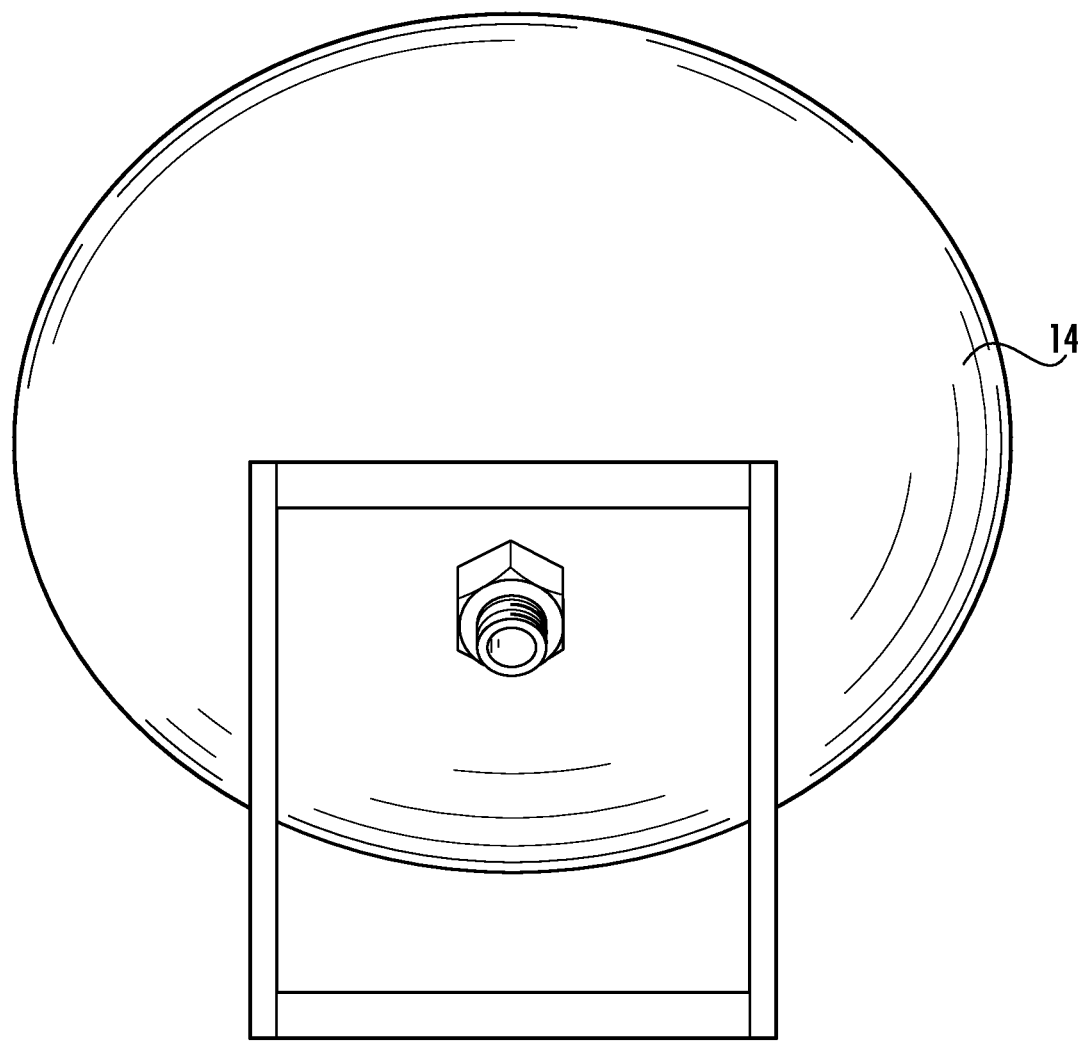
FIG. 6 illustrates a rear view of the solar energy concentrating mechanism shown in FIG. 4.

The exemplary solar radiation concentration mechanism 14 shown in FIG. 3 includes a receiver 16 that is operatively positioned relative to the concave dish 14 for receiving the concentrated solar thermal energy, and the HTL reactor 12a of the HTL system 12 is disposed within a housing of the receiver 16. In particular, as shown in FIGS. 3 through 5, the HTL reactor 12a comprises a coiled conduit disposed within the housing of the receiver 16. Thus, in this implementation, the thermal energy from the concentrated solar radiation is directly provided to the HTL reactor 12a. As shown in FIG. 3, the housing of the receiver 16 may be supported adjacent a surface of the concave dish 14 by one or more supports. As shown in FIG. 5, the support may include a post that includes threads for engaging a central portion of the dish 14. However, in other implementations, the HTL reactor 12a may be disposed remotely from the concave dish 14, and the concentrated solar thermal energy may be transferred to the HTL reactor 12a via a heat exchanger and a heat transfer fluid. The HTL system 12 may also include a pretreater (not shown).

The system 10 also includes a pump (not shown) that is configured for continuously pumping the biomass slurry through the HTL system 12. The pump may be configured for pumping the biomass slurry at a pressure around 20 MPa.

According to various implementations, wet biomass slurry is continuously pumped under high pressure through the HTL system 12. The biomass slurry is heated (directly or indirectly) by using the high energy beam focused by the solar thermal energy concentrating mechanism 14. In one implementation, the beam can reach about 1000° C. The subcritical water heated by the beam acts as a reaction solvent converting organic matter into biocrude. As shown in FIGS. 2 and 3, the organic fraction of the biomass is converted to biocrude and biogas, and the inorganic fraction is converted to biochar. In addition, an aqueous phase exits the HTL system 12, which can be treated by secondary treatment units of municipal biosolids treatment facilities or other suitable treatment methods.

Thus, the system 10 uses the thermal energy from the solar concentration mechanism 14 as the primary source of thermal energy for driving the HTL process, but secondary or backup sources of thermal energy may include combustion of biogas and/or natural gas. For example, the biogas may be captured from the HTL process or produced elsewhere and stored for use by the system 10. Combustion of the biogas and/or natural gas may be used to produce thermal energy on suboptimal solar days, for example. In addition, at least a portion of the thermal energy from the solar radiation concentration mechanism 12 and/or from the combustion of biogas and/or natural gas may be used by the generator to generate electricity. Furthermore, electricity may also be generated by using solar photovoltaic devices.

The thermal energy from the combustion of biogas and/or natural gas or from stored solar energy may be delivered to the HTL system 12 directly or indirectly via a heat transfer fluid and heat exchanger.

The system 10 may also includes a quencher (not shown) that is disposed adjacent an exit of the HTL system 12. The quencher quickly cools the biocrude to prevent degradation.

In addition, the system 10 may include a heat exchanger (not shown) downstream of the HTL system 12 that is configured for harvesting the heat energy from the biomass slurry. For example, the generator 16 may be configured for using this harvested heat energy for generating power for at least one of one or more biomass slurry pumps and one or more electrical components. In addition, the system 10 may further include a second HTL system (not shown) disposed downstream of the HTL system 12. The heat energy from the heat exchanger may be transferred to the second HTL system. In addition, the system 10 may include thermal and pressure-rated parts that are capable of withstanding the temperatures and pressures of the HTL process.

Figure 7:
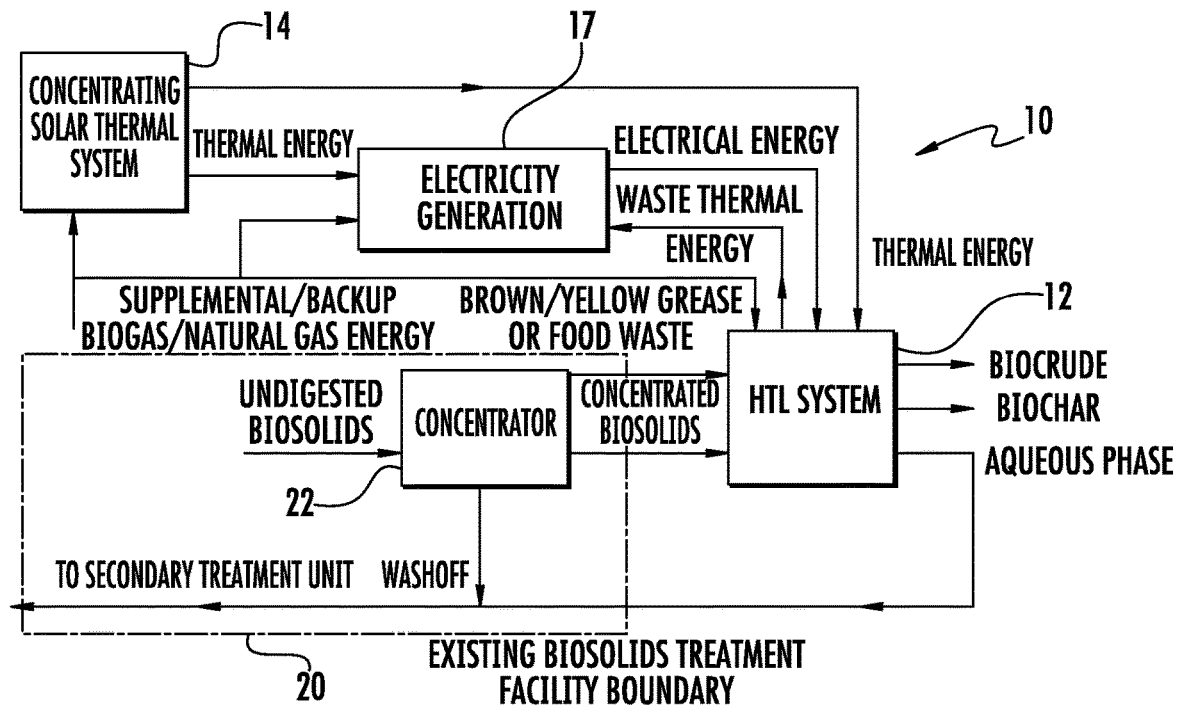
FIG. 7 illustrates a schematic diagram of the system of FIG. 2 being used with a biosolids treatment facility according to one implementation.

FIG. 7 illustrates an exemplary implementation of the system 10 of FIG. 2 being used with a new or an existing municipal biosolids treatment facility 20 according to one implementation. The system 10 further includes a biosolids concentrator 22 that receives undigested biosolids from the facility 20 and concentrates them. The concentrated biosolids are then received by the HTL system 12 for processing as described above in relation to FIG. 2. Washoff from the concentrator 22 is fed to a secondary treatment unit. The biosolids may include municipal biosolids, such as food waste and grease waste (e.g., yellow and/or brown grease waste).

Figure 8:
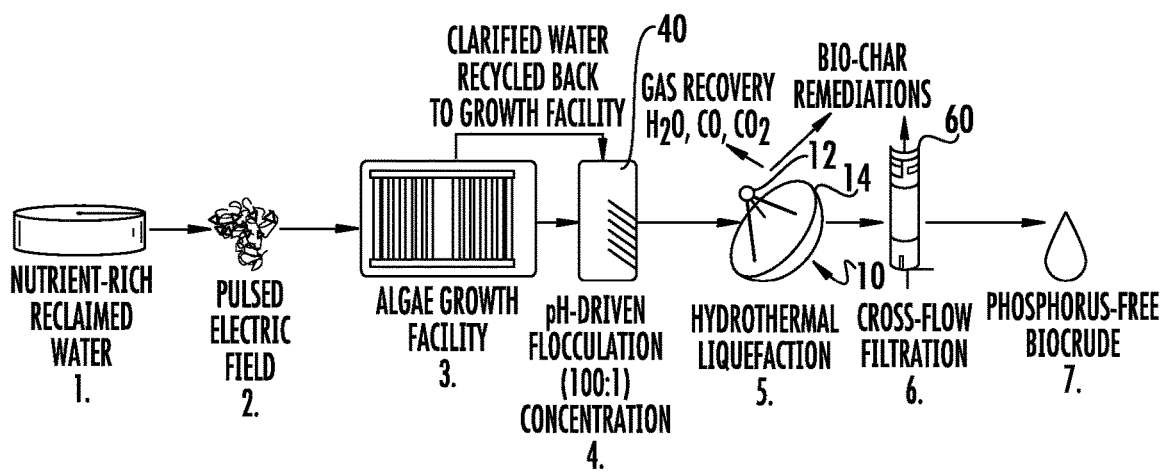
FIG. 8 illustrates a process of converting algae to biocrude using the system of FIG. 2 according to another implementation.

FIG. 8 illustrates an exemplary process of generating algae biomass feedstock and converting the algae feedstock to biocrude using the system of FIG. 2. In particular, in step 1, microalgae are cultivated using nutrient-rich waste streams. For example, microalgae may be cultivated in a bioreactor facility (e.g., 50,000 L vertical bioreactor facility). In step 2, the microalgae are passed through a pulsed electric field, which terminates micro-organismal contaminants. Then, in step 3, the microalgae are passed through an algae growth facility, and clarified water is recycled back to the growth facility. The microalgae are then passed through a pH-driven flocculation concentration mechanism 40 in step 4, in which NaOH concentrates dense algal biomass 100-fold without further drying. In step 5, the concentrated wet biomass is passed through the HTL reactor 12. NaOH serves as the catalyst in the HTL process as the wet biomass is passed through the thermal concentrator 14 of the HTL system 12. In step 6, the biocrude is subject to cross flow filtration through a filtration mechanism 60 whereby phosphorus and polar components are removed from the biocrude, increasing its stability. This process may be greater than 95% efficient. In step 7, the phosphorus-free biocrude is recovered.

Solar energy driven systems, such as system 10 described above in relation to FIGS. 2-8, provide large production capacity of converting biomass to biocrude, according to certain implementations. In addition, feeding the biomass through anaerobic digesters may not be necessary prior to subjecting the biomass to the HTL process.

According to other various implementations, municipal biosolids, grease waste, and food waste may be converted to renewable biocrude using biogas from anaerobic digesters as fuel for supplying the electrical and thermal energy required to produce the biocrude. Municipal biosolids, grease waste, and food waste pose a serious problem for water utilities for their proper treatment, discharge, and elimination. Currently, treatment facilities anaerobically digest part of the biosolid, grease, and food waste, but the facilities cannot eliminate it. The remaining portion is sent to landfills or sprayed onto large fields. In addition, facilities combust more than half of the biogas generated from their anaerobic digesters, which goes to waste. Thus, these implementations address at least two globally important problems of a growing population, namely: (i) biowaste reduction/utilization and (ii) renewable advanced biofuels generation. In addition, the process is energy self-sufficient and uses a reliable feedstock for consistently producing a reliable source of biocrude, which are major barriers for biocrude production with other technologies.

Figure 9:
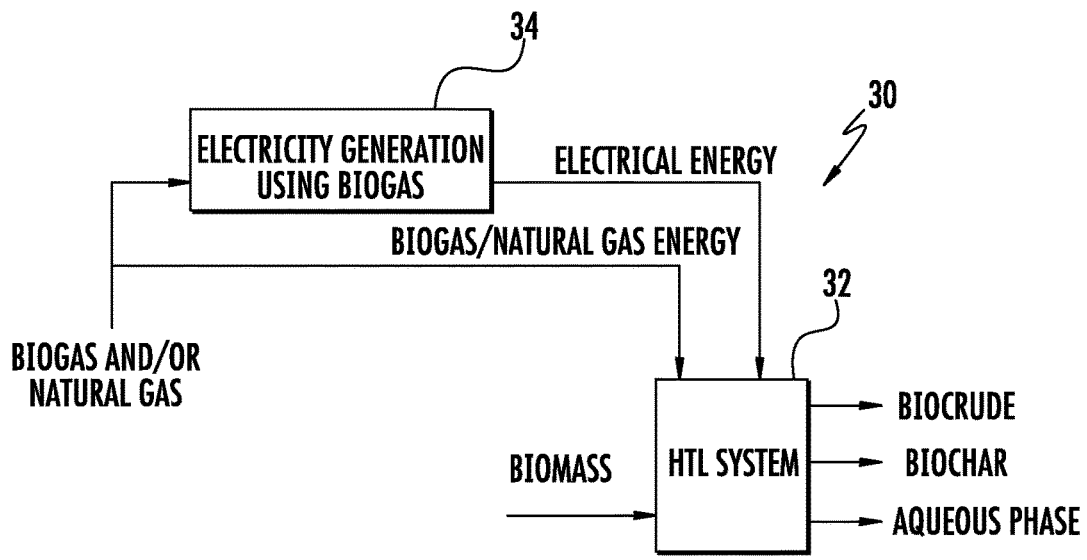
FIG. 9 illustrates a schematic diagram of an HTL system that uses biogas to provide thermal energy to the HTL reactor according to certain implementations.

FIG. 9 illustrates an exemplary schematic diagram of a system 30 for converting biosolids and grease and food waste to biocrude using thermal energy from combusted biogas according to one implementation. In particular, the system includes an HTL system 32 and a generator 34 that uses thermal energy from combusted biogas and/or natural gas to generate power. The biogas (or natural gas as a backup) is combusted and the thermal energy is used by the generator 34 to generate electricity for the HTL system 32 and other electrical components of the system 30. The thermal energy from the combustion of the biogas is also transferred to the HTL system 32 to assist with the production of biocrude. As noted above, the HTL system 32 may include a pretreater and a reactor. Concentrated biosolids, grease or food waste, or other types of biomass feedstock are fed to the HTL system 32 and are converted by the HTL system 32 to biocrude, biochar, and an aqueous phase. Furthermore, any biogas resulting from the HTL process may be rerouted back to the generator 34 or the HTL system 32 for combustion or to recover the waste heat carried by the biogas. The biosolids and biogas may be supplied at the same location as the system 30 or may be produced elsewhere and transferred to the system 32. For example, when the system is implemented at a new or an existing biosolids treatment facility, such as is described below in relation to FIG. 10, the biogas and biosolids are provided on site. In addition, natural gas may be provided as a secondary or backup source of thermal energy.

Figure 10:
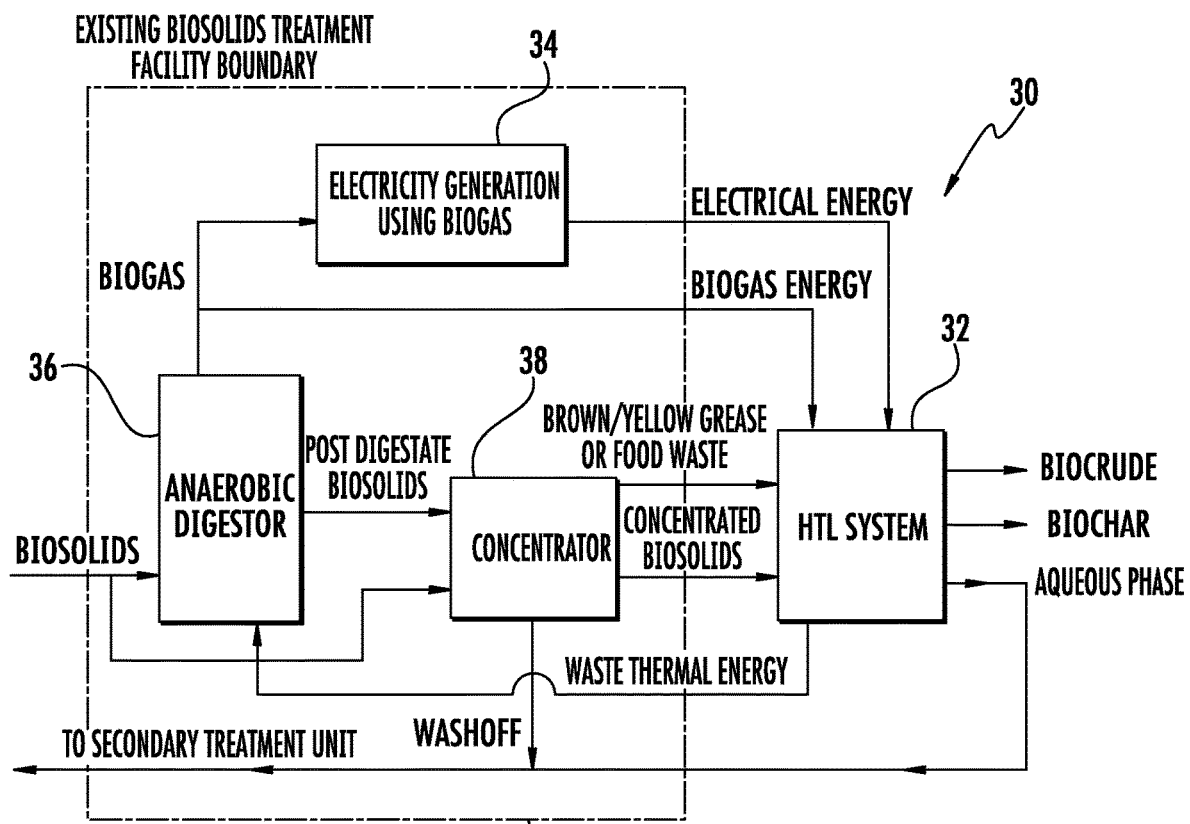
FIG. 10 illustrates a schematic diagram of the system of FIG. 9 being used with a biosolids treatment facility according to one implementation.

FIG. 10 illustrates an exemplary implementation of the system 30 in a new or an existing municipal biosolids treatment facility 40. The facility 40 includes at least one anaerobic digester 36 and at least one biosolids concentrator 38. At least a portion of the biosolids may be fed to the anaerobic digester 36, and the digested (and any undigested) biosolids are fed to the concentrator 38. The concentrated biosolids are then fed to the HTL system 32 and converted to biocrude, biochar, and the aqueous phase as described above in relation to FIG. 9. The aqueous phase may be fed to secondary or tertiary treatment units of the biosolids treatment facility for further processing. Biogas produced by the anaerobic digester 36 is combusted, and the resulting thermal energy is used by the generator 34 for generating electricity and by the HTL system 32 for the biosolid to biocrude conversion process. Furthermore, waste thermal energy from the HTL system 32 may be transferred to the anaerobic digester 36 to assist with the digestion process or the generator 34.

In some implementations, the anaerobic digester 36 may be configured to generate more hydrogen, which can be separated from the biogas. In addition, the biocrude may be fed upstream of the HTL system 32 to an upgrading unit (not shown) to remove nitrogen and sulfur from the biocrude.

Figure 11:
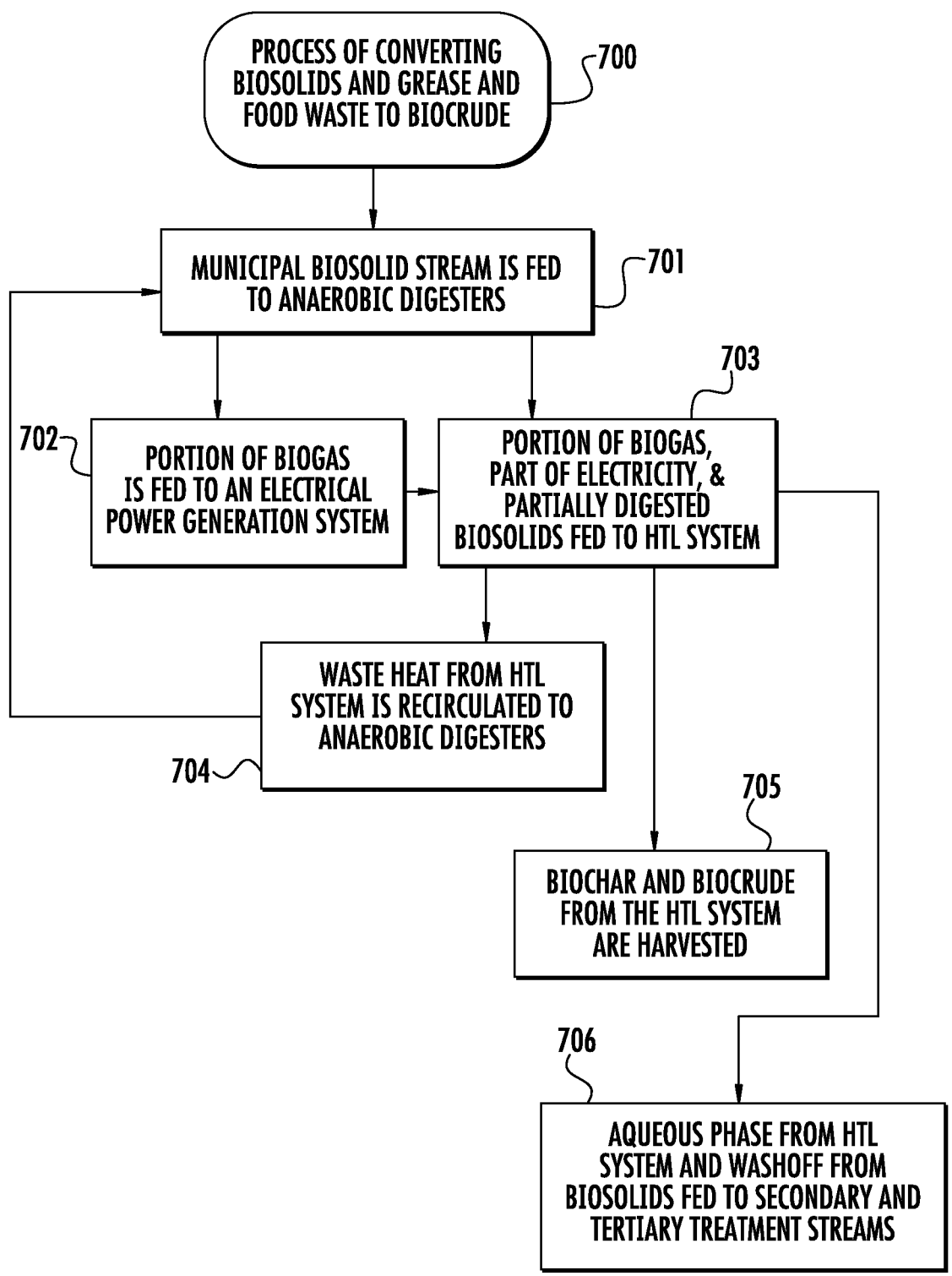
FIG. 11 illustrates a process of converting biosolids to biocrude using the system of FIG. 10 according to one implementation.

FIG. 11 illustrates an exemplary continuous flow process 700 of converting biosolids and grease and food waste to biocrude according to the implementation shown in FIG. 10. Starting at step 701, a municipal biosolid stream is fed to anaerobic digesters 36. The digesters 36 generate biogas from partial digestion of biosolids. At step 702, a portion of this biogas is fed to the electrical power generator 34. At step 703, the remaining biogas, part of the generated electricity, and the partially digested biosolids effluent from the digesters 36 are fed to the HTL system 32. The HTL system 32 features a pretreater and a reactor. Then, in step 704, the waste heat from the HTL system 34 is recirculated to the anaerobic digesters 36. In step 705, biochar and biocrude from the HTL system 36 are harvested as the main products. In step 706, the aqueous phase from the HTL system 36 and the washoff from the preconcentration of the biosolids are fed to the secondary and/or tertiary treatment streams of the biosolids treatment plant 40. In addition, the waste heat from the generator 34, which may be about 450° to 650° C., to supply the thermal energy needs of the HTL and use the waste heat from the HTL to supply the thermal energy needs of the anaerobic digesters.

According to certain implementations, high pressure and high temperature-rated parts are used in the system due to the high temperature and high pressure environment. In addition, the aqueous phase may be further processed to form a third stream of product, for example, fertilizer supplement, according to some implementations. Furthermore, other sources of biowaste, such as brown or yellow grease and food waste, may be used used in the process 700 according to some implementations.

Figure 12:
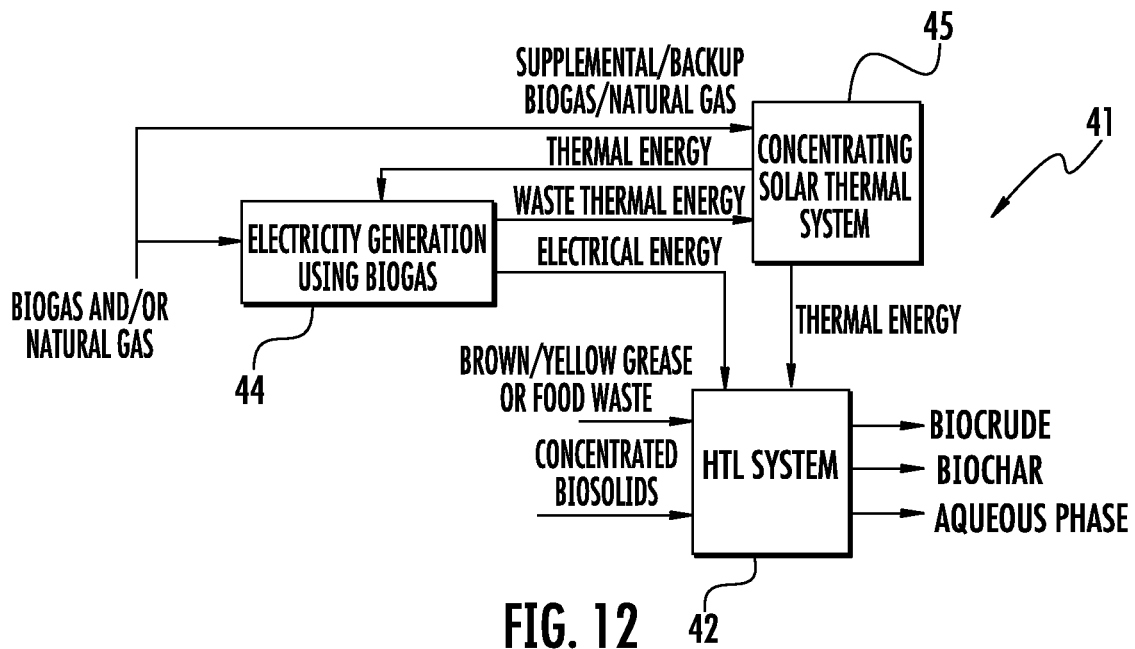
FIG. 12 illustrates a schematic diagram of an HTL system that uses a combination of biogas and a solar radiation concentration mechanism to provide thermal energy to the HTL reactor according to certain implementations.

Other sources of thermal and/or electrical energy may be used for the HTL system, such as energy from photovoltaic panels, biogas from landfislls, inexpensive natural gas, concentrating solar thermal systems, such as the solar thermal system described above in relation to FIGS. 2-8, or combinations thereof, according to certain implementations. For example, FIG. 12 illustrates a schematic diagram of a hybrid system 41 that uses thermal energy from biogas (and/or natural gas) combustion and from solar radiation. In this system 41, either source of thermal energy may serve as a primary source with the other serving as a secondary source, or substantially equal portions of thermal energy produced may each process may be used to drive the HTL process, according to certain implementations. The system 41 includes an HTL system 42, a concentrating solar thermal system 45, such as photovoltaic panels, parabolic mirrors, Fresnel lens, or concave dishes (e.g., the dish shown in FIGS. 3-6), and a power generator 44 that receives thermal energy from biogas (and/or natural gas) combustion and the solar thermal system 45. The waste heat from the generator 44 may be transferred via a heat exchanger and heat transfer fluid to the solar thermal system 45, and thermal energy from the solar thermal system 45 may be directly or indirectly provided to the HTL system 42, as described above in relation to FIGS. 2-8. Electrical energy from the generator 44 is also used by the HTL system 42. Concentrated and/or unconcentrated biosolids and/or food or grease waste are fed to the HTL system 42, and after processing, biocrude, biochar, and the aqueous phase are produced by the HTL system 42. As noted above, the HTL system 42 may include a pretreater and a reactor.

Figure 13:
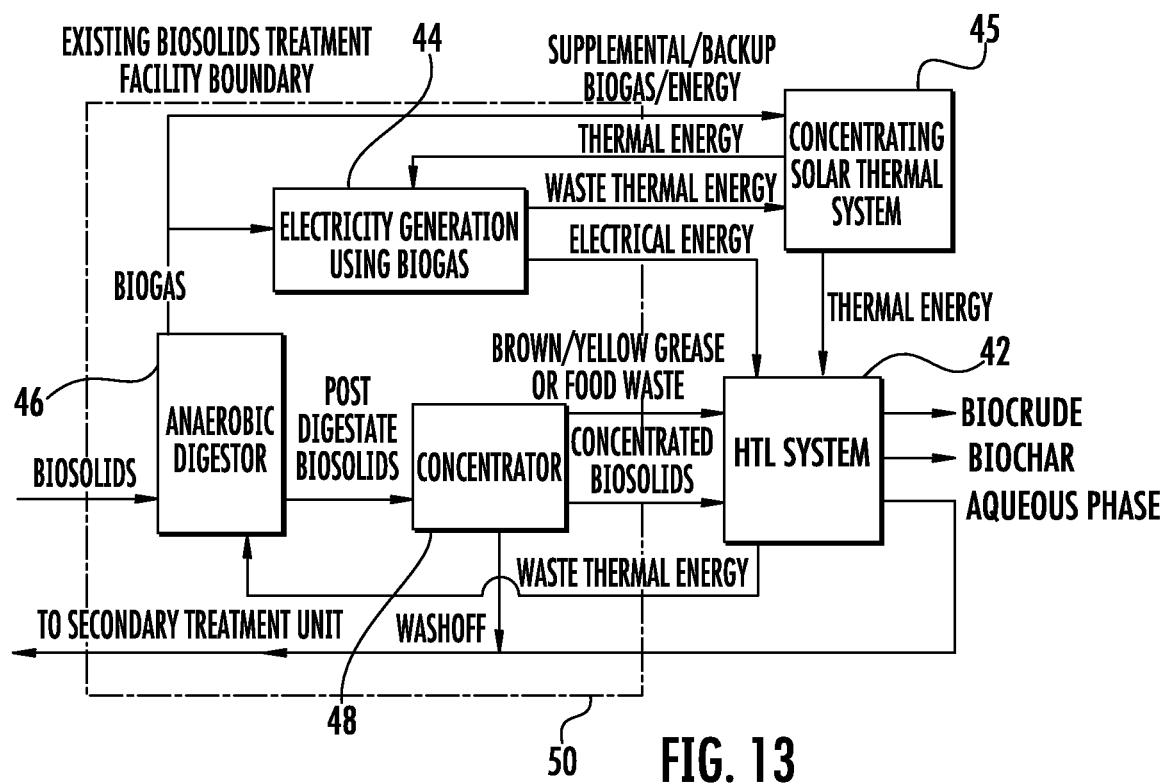
FIG. 13 illustrates a schematic diagram of the system of FIG. 12 being used with a biosolids treatment facility according to one implementation.

FIG. 13 illustrates an exemplary implementation of the hybrid system 41 shown in FIG. 12 as used in a new or an existing municipal biosolids treatment facility 50. The facility 50 includes at least one anaerobic digester 46 and at least one concentrator 48. The biosolids are fed to the anaerobic digester 46, and biogas resulting from the digestion process is combusted and/or stored. The digested biosolids are fed to the concentrator 48, and the concentrated biosolids are then fed to the HTL system 42. The waste thermal energy from the HTL system 42 may transferred to to the anaerobic digester 46. In addition, the aqueous phase and washoff from the concentrator 48 may be fed to the secondary and/or tertiary treatment units for further processing.

Municipal biosolids have high organic content for biocrude production, are pre-collected and concentrated at treatment plants, do not require extra energy or effort for collection, and are likely to be consistently and increasingly available over time as populations grow. The biogas produced in anaerobic digesters from biosolids is an excellent source of fuel that may be generated on-site for supplying the electrical and thermal energy required to produce biocrude. In addition, the above described process and production system readily integrate into an existing biosolids treatment facility, providing a pathway for cost-effective biocrude production.

As noted above, one of the main barriers to the widespread application of the HTL process is that the energy necessary to create a subcritical water environment (high temperature, high pressure) to drive the biomass-to-biocrude conversion process exceeds the energy available in the biocrude product, creating a negative EROI. The thermal energy collected by the solar energy concentration mechanism and/or the combustion of biogas and/or natural gas of the systems and processes described above provides heat energy in excess of that necessary to create a subcritical water state. In addition, the systems and processes described herein provide an engineered continuous flow that facilitates the high heat, high pressure conditions necessary to drive the HTL reaction forward (converting biomass to biocrude). This coupled process, unlike other HTL processes, produces a positive EROI and thus a pathway to cost-effective biomass-to-biocrude production on any scale.

The system allows for use of a variety of biomass and/or biowaste feedstocks in the process, including municipal biosolids, food waste, animal waste, grease waste, cellulosic waste, as well as microalgae. This facilitates recycling of waste materials that may have otherwise been subject to disposal in a land-fill.

Advantages of one or more implementations of the systems and methods described herein include: (1) continuous flow, (2) comparatively high biomass-to-biocrude yields, (3) nearly free energy input capable of generating a positive EROI for the process, (4) recycling of organic waste materials to renewable biocrude, (4) energy self-sufficiency, (5) use of a reliable biowaste feedstock that is low cost and is likely to increase in amount over time with growing populations, (6) the ability to implement the system in developed and under-developed countries, (7) applicability to a wide variety of biomass feedstocks, and (8) easily scalable.

The invention claimed is:

1. A system for converting biomass to biocrude comprising:
a hydrothermal liquefaction system comprising a hydrothermal liquefaction reactor, the hydrothermal liquefaction reactor configured for receiving biomass feedstock and converting the biomass feedstock to biocrude, wherein the hydrothermal liquefaction system receives biogas and combusts the biogas to provide thermal energy to the hydrothermal liquefaction reactor.

2. The system of claim 1, further comprising at least one anaerobic digester configured for digesting biowaste and producing the biogas.

3. The system of claim 2, wherein the biomass feedstock received by the hydrothermal liquefaction reactor comprises the biowaste digested by the anaerobic digester, and the system further comprises a concentration mechanism configured for receiving the biosolids biowaste from the anaerobic digester and concentrating the biowaste prior to the biowaste being converted to biocrude by the hydrothermal liquefaction reactor.

4. The system of claim 3, wherein the system is configured for being installed at least partially within a biosolids treatment facility.

5. The system of claim 2, wherein the biowaste comprises municipal biosolid waste, grease waste, and/or food waste.

6. The system of claim 1, wherein the biogas is harvested remotely from the system.

7. The system of claim 1, wherein the biogas for combusting by the hydrothermal liquefaction system is a first portion of biogas, and the system further comprises a generator configured for receiving thermal energy from combustion of a second portion of biogas, the generator configured for generating electrical energy, wherein the generated electrical energy and any remaining thermal energy from the combustion of the second portion of biogas are provided to the hydrothermal liquefaction reactor for heating the biomass feedstock.

8. The system of claim 1, wherein the biomass feedstock comprises biowaste.

9. The system of claim 8, wherein the biowaste comprises municipal biosolid waste, grease waste, and/or food waste.

10. The system of claim 1, wherein the biomass feedstock comprises algae and/or marine biomass.

11. The system of claim 1, wherein the biomass feedstock comprises wood waste.

12. The system of claim 1, wherein the biomass feedstock comprises cellulosic waste.

13. The system of claim 1, further comprising a pump configured for continuously pumping the biomass feedstock through the hydrothermal liquefaction reactor.

14. The system of claim 13, wherein the pump is configured for pumping the biomass feedstock at a pressure around 20 MPa.

15. The system of claim 1, further comprising a quencher disposed adjacent an exit of the hydrothermal liquefaction reactor, the quencher configured for quickly cooling the biocrude.

16. The system of claim 1, further comprising a heat exchanger downstream of the hydrothermal liquefaction reactor, the heat exchanger configured for harvesting the thermal energy from combustion of the biocrude, biogas, and/or biochar produced by the hydrothermal liquefaction reactor.

17. The system of claim 16, further comprising a generator configured for generating electrical energy for operating at least one of one or more pumps and one or more electrical components, wherein the thermal energy from the heat exchanger is used for driving the generator.

18. A process of converting biomass feedstock to biocrude comprising:
    combusting biogas, by a hydrothermal liquefaction system, to produce thermal energy;
    pumping biomass feedstock through a hydrothermal liquefaction reactor of the hydrothermal liquefaction system; and
    heating, in the hydrothermal liquefaction reactor, the biomass feedstock using the thermal energy from the combustion of the biogas.

19. The process of claim 18, wherein the biogas is produced by at least one anaerobic digester of a biosolids treatment facility.

20. The process of claim 18, further comprising: collecting thermal energy from combustion of natural gas; and heating the biomass feedstock using the collected thermal energy from the combustion of natural gas in the hydrothermal liquefaction reactor.

21. A process of converting biomass to biocrude, comprising:
    feeding municipal sludge to at least one anaerobic digester, the municipal sludge comprising biowaste;
    collecting thermal energy from combustion of a first portion of biogas generated from partial digestion of the biowaste;
    providing the thermal energy from combustion of the first portion of biogas to a generator;
    providing a second portion of biogas generated from partial digestion of the biowaste to a hydrothermal liquefaction system for combusting, the hydrothermal liquefaction system comprising a hydrothermal liquefaction reactor;
    providing the thermal energy from combustion of the second portion of the biogas, waste heat generated by the generator, at least a portion of electrical energy generated by the generator, and the partially digested biowaste from the anaerobic digester to the hydrothermal liquefaction reactor;
    recirculating waste heat generated by the hydrothermal liquefaction system to the anaerobic digesters; and
    harvesting biocrude from the hydrothermal liquefaction system.

22. The process of claim 21, further comprising concentrating the partially digested biowaste fed from the anaerobic digester prior to feeding the partially digested biowaste to the hydrothermal liquefaction reactor, and feeding an aqueous phase from the hydrothermal liquefaction reactor and washoff from the concentration of the partially digested biowaste to secondary and tertiary treatment streams of a biosolids treatment plant.

23. The process of claim 21, further comprising harvesting waste thermal energy from the hydrothermal liquefaction system and providing the waste thermal energy to an electrical generator and/or the at least one anaerobic digester.

24. The system of claim 1, wherein the biomass feedstock comprises animal waste.

* * * * *

UNITED STATES PATENT AND TRADEMARK OFFICE
CERTIFICATE OF CORRECTION

PATENT NO.        : 10,551,060 B2
APPLICATION NO.   : 15/791061
DATED             : February 4, 2020
INVENTOR(S)       : Halil Berberoglu et al.

Page 1 of 1

It is certified that error appears in the above-identified patent and that said Letters Patent is hereby corrected as shown below:

In the Claims

Column 10, Line 45, delete "...for receiving the biosolids biowaste from the..." and insert -- "...for receiving the biowaste from the..." --, therefor.

Signed and Sealed this
Fourth Day of August, 2020

Andrei Iancu
*Director of the United States Patent and Trademark Office*